(12) United States Patent
Kato

(10) Patent No.: US 8,630,389 B2
(45) Date of Patent: Jan. 14, 2014

(54) X-RAY IMAGING APPARATUS

(75) Inventor: Katsushi Kato, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 90 days.

(21) Appl. No.: 13/211,037

(22) Filed: Aug. 16, 2011

(65) Prior Publication Data

US 2011/0299660 A1    Dec. 8, 2011

Related U.S. Application Data

(63) Continuation of application No. 12/537,118, filed on Aug. 6, 2009, now Pat. No. 8,019,045.

(30) Foreign Application Priority Data

Aug. 8, 2008  (JP) ................................. 2008-205689

(51) Int. Cl.
*H05G 1/54*    (2006.01)

(52) U.S. Cl.
USPC ......................................................... 378/116

(58) Field of Classification Search
USPC ........................... 378/4–20, 62, 116, 193–197
See application file for complete search history.

(56) References Cited

U.S. PATENT DOCUMENTS 8,019,045 B2 *  9/2011  Kato ............................. 378/116

FOREIGN PATENT DOCUMENTS

| JP | 2001145616 A | 5/2001 |
| WO | 2008035953 A1 | 3/2008 |

* cited by examiner

*Primary Examiner* — Courtney Thomas
(74) *Attorney, Agent, or Firm* — Canon USA Inc. IP Division

(57) ABSTRACT

An X-ray imaging apparatus includes an imaging unit which is rotatable relative to a platform about a shaft portion perpendicular to an X-ray detecting surface, so as to change the orientation relative to a subject.

17 Claims, 8 Drawing Sheets

X-RAY IMAGING APPARATUS

CROSS REFERENCE TO RELATED APPLICATIONS

This application is a CONTINUATION of prior U.S. patent application Ser. No. 12/537,118 filed Aug. 6, 2009, which claims priority from Japanese Patent Application No. 2008-205689 filed on Aug. 8, 2008, the disclosures of which are hereby incorporated by reference herein in their entirety.

BACKGROUND OF THE INVENTION

1. Field of the Invention

The present invention relates to X-ray imaging apparatuses for acquiring X-ray images from X-rays transmitted through imaging subjects.

2. Description of the Related Art

In an X-ray imaging apparatus in general, an X-ray generator and an imaging unit containing an X-ray detector are disposed so as to face each other, and imaging is performed by arranging a subject to be imaged such as a human body between the X-ray generator and the imaging unit. In X-ray imaging, a position of the imaging unit relative to the X-ray generator and the subject is determined and then the subject is irradiated with X-rays to obtain necessary X-ray images.

With the recent advances in the speed of image processing apparatuses, apparatuses capable of capturing moving images and three-dimensional images in addition to two-dimensional still images have gradually become commercially available. To obtain three-dimensional images, dedicated computed tomography apparatuses (CT apparatuses) are generally used. Recently, however, cone beam CT (CBCT) has also come to be in practical use. In CBCT, an image intensifier (I.I.) and a two-dimensional sensor such as a flat panel detector are used for obtaining a three-dimensional image from two-dimensional images by calculation. CBCT utilizes relative movement between an imaging system and the subject, so that a number of two-dimensional X-ray projection images are obtained and cross-sectional images and three-dimensional images are generated by calculation based on the two-dimensional X-ray images.

In CBCT imaging which utilizes a C-Arm imaging apparatus, an X-ray generator and an imaging unit rotate around the subject supported by an subject support such as a bed, so that X-ray projection images of the subject viewed at various angles are obtained. In a CBCT imaging technique disclosed in Japanese Patent Laid-Open No. 2000-116635, X-ray projection images of the subject corresponding to various angles are obtained by irradiating the subject with X-rays while the subject is being rotated and supported by a turntable. Further, Japanese Patent Laid-Open No. 2006-75236 discloses an apparatus which can be used for both CBCT imaging and general X-ray still imaging.

However, in X-ray imaging in general, imaging operations are performed by positioning a subject as close to the imaging unit as possible or bringing the chest or chin of the subject into contact with the outer surface of the imaging unit. This is because sharper images that are less influenced by blurring due to scattered radiation can be acquired with decreasing distance between the X-ray detector of the imaging unit and the subject. In particular, when a still image of the chest of the subject is captured, it is preferable that an imaging operation be performed while the body section from the chest to the shoulders remains in contact with the front surface of the imaging unit and each arm be positioned along the side and back surfaces of the imaging unit. Thus, there is a number of imaging apparatuses provided with handrails along the side and back surfaces of imaging units.

An X-ray beam emitted from an X-ray tube is focused onto an area effective for imaging, after its unnecessary part is removed by an X-ray limiting device. Usually, the X-ray limiting device is set such that an image acquiring area of the X-ray detector generally coincides with the X-ray irradiation range. X-rays are applied to a space in the shape of a pyramid, quadrangular pyramid in many cases, with its vertex at the end of the X-ray tube and its bottom on the detecting surface of the X-ray detector, and thus projection images corresponding to the area are acquired.

Since an X-ray beam travels radially outward, the size of an image of the subject projected on the X-ray detecting surface becomes larger than the actual size as the distance between the imaging unit and the subject increases. In general X-ray imaging in which the subject is brought into contact with the imaging unit, a nearly full-scale image can be obtained, which is effective to include all necessary parts of the subject in a limited image acquiring area of the X-ray detector.

On the other hand, in CBCT imaging, relative movement is utilized as mentioned above. Thus, it is necessary to keep a certain amount of distance between the imaging unit and the subject in order to reduce the risk of collision between the imaging unit and the subject. As the distance increases, the magnification of projection of the subject on the X-ray detecting surface increases. Thus, in order to include the all necessary parts of the subject, large dimensions of the detecting surface of the X-ray detector are necessary.

Further, in reconstruction of cross-sectional images in CBCT imaging, accurate cross-sectional image data may not be obtained without all projection data of cross sections of the entire body which are orthogonal to the body axis (longitudinal axis) of the subject. Thus, there is a great need for an X-ray imaging apparatus in which the dimension of the image acquiring area in the direction of the shoulders is particularly large relative to the dimension in the direction of the longitudinal axis of the subject. To meet this need, the transverse dimension of an X-ray detector may increase so as to be suitable for CBCT imaging. With this increase, as a result, the transverse dimension of the imaging unit also increases.

When a general X-ray imaging operation is performed to obtain an image of the chest of a patient having a small body and narrow shoulders, for example, it is difficult to place the arms of the subject along the side and back surfaces of the imaging unit. As a result, in many cases, a body section from the chest to the shoulder fails to contact the front surface of the imaging unit. In addition, for a patient who is not able to grab handrails provided on the back surface of the imaging unit, it is difficult to stabilize his or her body posture, which brings difficulty in obtaining a satisfactory image.

Thus, there is incompatibility in that the detection area of an X-ray detector preferably has a large transverse dimension in CT imaging for obtaining cross-sectional images and three-dimensional images, and the housing of an imaging unit preferably has a small transverse dimension for capturing a still image of the chest.

SUMMARY OF THE INVENTION

The present invention has been made in view of the above circumstances. Accordingly, there is a need for an X-ray imaging apparatus capable of both CT imaging and still imaging under desirable imaging conditions.

An X-ray imaging apparatus according to an exemplary embodiment of the present invention includes a driving unit and a control unit for relatively rotating an X-ray imaging system composed of an X-ray generator and an X-ray detector around a subject and is capable of both computed tomographic (CT) imaging and still imaging, wherein the X-ray detector has a detection area having the shape of a flat rectangle with short sides and long sides, and the X-ray detector selects any one from among at least two orientations including a first orientation in which the long sides of the detection area are parallel to a longitudinal axis of the subject and a second orientation in which the short sides of the detection area are parallel to the longitudinal axis of the subject.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

Preferred exemplary embodiment of the present invention will be described in detail in accordance with the accompanying drawings.

Figure 1:
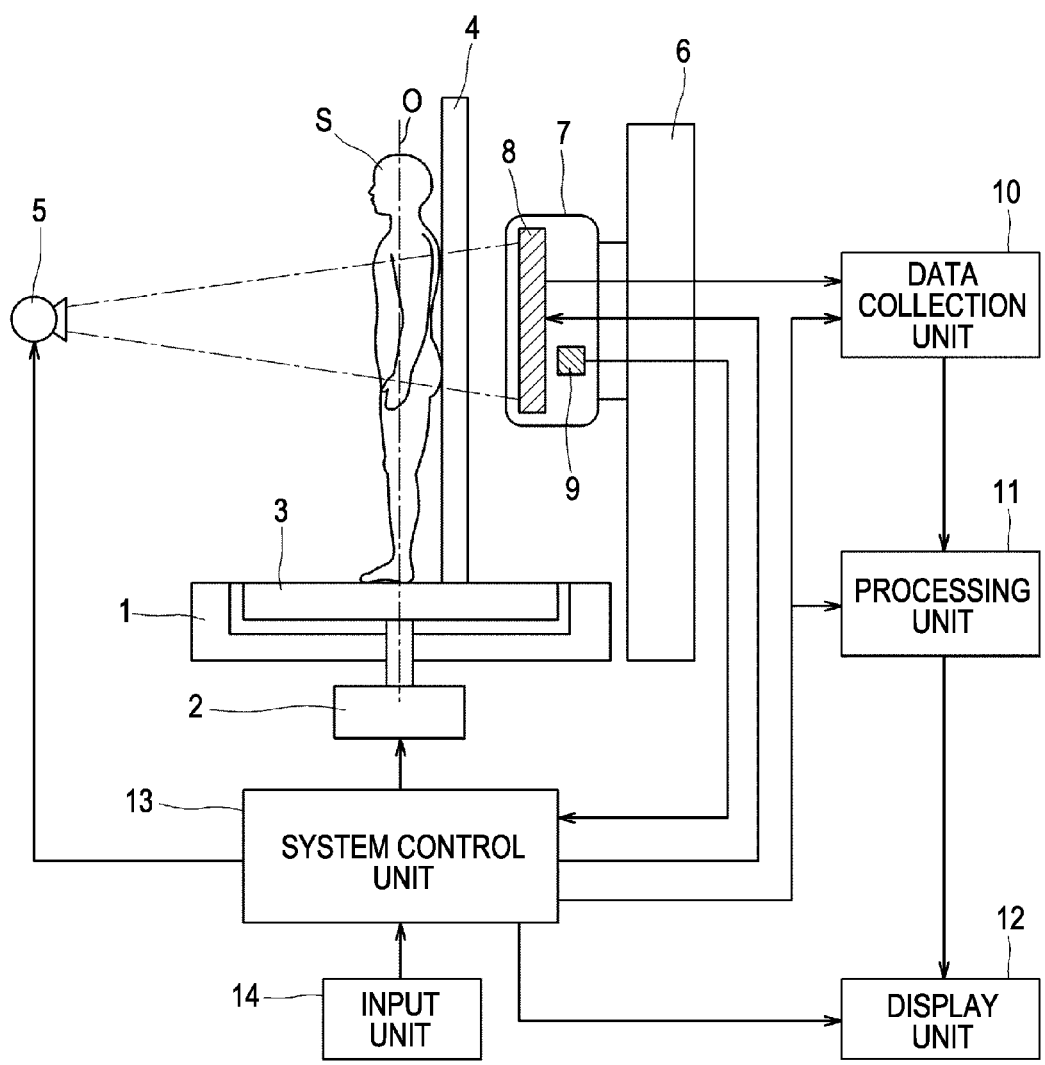
FIG. 1 illustrates a CT mode of an X-ray imaging apparatus according to an exemplary embodiment of the present invention.

FIG. 1 illustrates CT (computed tomographic) imaging performed by an X-ray imaging apparatus according to an exemplary embodiment of the present invention. A subject mount 1 has a turntable 3 mounted thereon which serves as rotation driving means driven by a driving unit 2. The turntable 3 is disposed so as to be rotatable about a rotation center O and is provided with a detection mechanism (not shown) for detecting the angle, position and the rotation speed of the turntable 3. The driving unit 2 supplies torque to the turntable 3, enabling starting, acceleration, deceleration, and stopping of the turntable 3. A subject supporting member 4 is disposed on the turntable 3 for supporting and fixing a subject S at a position which generally coincides with a rotation axis O. A part of the subject supporting member 4 corresponding to an X-ray irradiation area is fabricated with a material having a high X-ray transmittance.

An X-ray tube 5 serving as X-ray generating means is supported by a supporting mechanism (not shown) and arranged in front of the subject S. The X-ray tube 5 is configured such that the position of an X-ray beam such as the direction and height can be adjusted. An imaging unit 7 is supported by a platform 6 located behind the subject S via a mechanism permitting at least up-and-down movement and a rotation mechanism which will be described below. The imaging unit 7 contains an X-ray detector 8 for detecting an X-ray image and an imaging unit orientation detector 9 for detecting an orientation of the imaging unit 7. The X-ray detector 8 is composed of a scintillator a photodetector, electric circuits, and the like, which are known in the art. The X-ray tube 5 and the X-ray detector 8 are disposed so as to face each other forming an X-ray imaging system.

An output of the X-ray detector 8 is connected to a data collection unit 10 for storing X-ray image data. An output of the data collection unit 10 is connected to a display unit 12 via a processing unit 11 for performing operation processing on image data. The display unit 12 displays a processed image and may be a device such as a computer display in general. However, the display unit 12 may be another electric display, an audio message transmitter or the like, or a combination thereof to achieve similar effects.

The X-ray imaging apparatus is also provided with a system control unit 13 for integrally controlling the entire apparatus. An output of the system control unit 13 is connected to the driving unit 2, the X-ray tube 5, the X-ray detector 8, the data collection unit 10, the processing unit 11, and the display unit 12. The system control unit 13 is also connected to outputs of the imaging unit orientation detector 9 and an input unit 14 for instructing selection of imaging mode, setting of parameters, initiation of an imaging operation, and the like.

When CT imaging is performed, X-rays are emitted from the X-ray tube 5 toward the subject S being rotated by the driving unit 2, so that X-ray images corresponding to individual rotation angels are detected by the X-ray detector 8 and the images are processed based on instructions provided by the system control unit 13.

Figure 2:
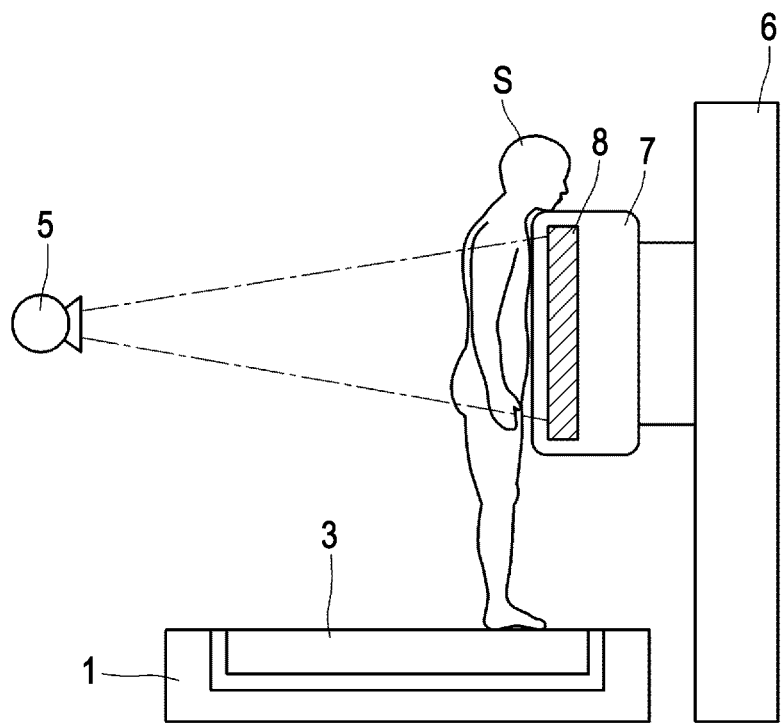
FIG. 2 illustrates a still image mode.

FIG. 2 illustrates a still image mode, which is another form of imaging performed by the X-ray imaging apparatus. In this still image mode, the subject supporting member 4 used in the CT mode illustrated in FIG. 1 may be removed or temporarily taken away. After the subject supporting member 4 is removed, the subject S is made to stand close to the imaging unit 7, so that a still image of an arbitrary part of the whole body of the subject S can be captured.

Since X-rays emitted from the X-ray tube 5 travel outward forming a conical shape, it is generally preferable that the subject S be positioned close to the imaging unit 7 to the extent that the subject S comes into contact with the imaging unit 7. When the position of the subject S is the closest to the X-ray detector 8, maximum use of the detection area of the X-ray detector 8 can be attained, and an image with a satisfactory resolution can be obtained.

Figure 3:
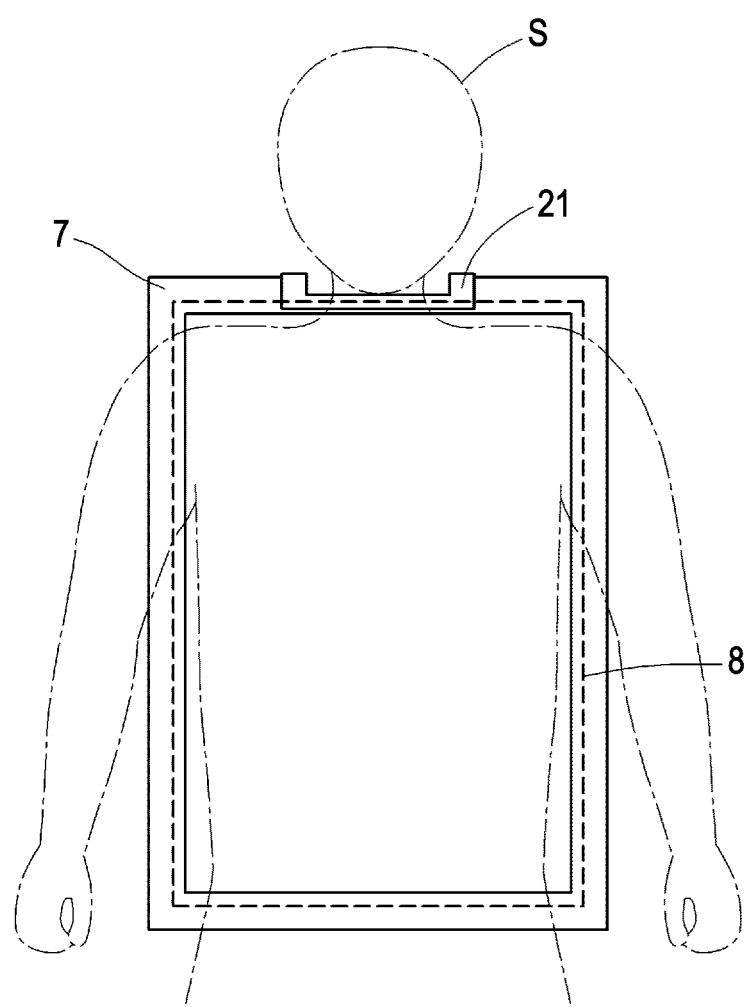
FIG. 3 is an elevational view of an imaging unit.

FIG. 3 is an elevational view of the imaging unit 7 as viewed from the X-ray tube 5 in the still image mode, in which a dotted-chain line indicates the subject S. A chin rest 21 is provided at the center of the upper short side of the imaging unit 7 for direct contact with the chin of the subject S. For example, the chin rest 21 may be formed of a material other than a metal to prevent discomfort from coldness and may have a shape which facilitates wiping off for disinfection. In addition, the chin rest 21 may be provided in the form of a depression in the edge of the imaging unit 7. This prevents intervention between the chin of the subject S and the housing of the imaging unit 7 and allows the shoulder part of the subjects S to be included in the detection area.

The arrangement illustrated in FIG. 3 is most appropriate for still imaging for obtaining an X-ray image of the chest of the subject S, especially the lung field. The X-ray detector 8 indicated by a broken line is a flat solid state detector contained in the imaging unit 7. In the X-ray detector 8, X-ray detecting devices formed of pixels and thin film transistors (TFTs) are arrayed in a two-dimensional matrix.

In general, X-ray detectors have rectangular detection areas in view of the efficiency of arrays. Although there are some X-ray detectors having square detection areas, the X-ray detector 8 according to an exemplary embodiment of the present invention includes a flat, rectangular detection area having long sides and short sides. The outer shape of the X-ray detector 8 also has the shape of a rectangle having long sides and short sides, in accordance with the shape of the detection area. Similarly, the imaging unit 7 containing the X-ray detector 8 and the detection area has a rectangular outer shape having long sides and short sides. This is for the purpose of increasing the degree of freedom in imaging operations by making unnecessary parts other than the detection area as small as possible.

The difference in the side lengths (i.e., long sides and short sides) of the outer shapes of the X-ray detection area of the X-ray detector 8 and the imaging unit 7 can solve incompatibility between the need for a large transverse dimension of the detection area in CT imaging operations and the need for a small transverse dimension of the detection area in still imaging operations, by rotating the imaging unit 7 and the X-ray detector 8 by 90 degrees.

When still imaging of the chest is performed, the orientation of the imaging unit 7 is set to a first orientation, in which the long sides of the detection area of the X-ray detector 8 is set to be parallel to the body axis (longitudinal axis) of the subject S. In CBCT imaging, the orientation of the imaging unit 7 is set to a second orientation, in which the short sides of the detection area of the X-ray detector 8 are parallel to the longitudinal axis of the subject S. This arrangement can solve the incompatibility mentioned above. Note that the imaging unit 7 may be set to the second orientation even in the case of still imaging, depending on the body section to be imaged and the orientation of the subject S.

In still imaging of the chest, in order to effectively include the lung field within the detection area, the dimension of the detection area in the direction of the shoulders (transverse dimension) needs to be at least 350 mm. In addition, as described above, when the subject S has a small body, an excessively large transverse dimension is not desirable considering the intervention between the imaging unit 7 and the shoulders and arms of the subjects. On the other hand, an increase in the dimension of the imaging unit 7 in the direction of the longitudinal axis does not cause problems, since there is not restriction other than the intervention of the chin rest 21 mentioned above.

Figure 4:
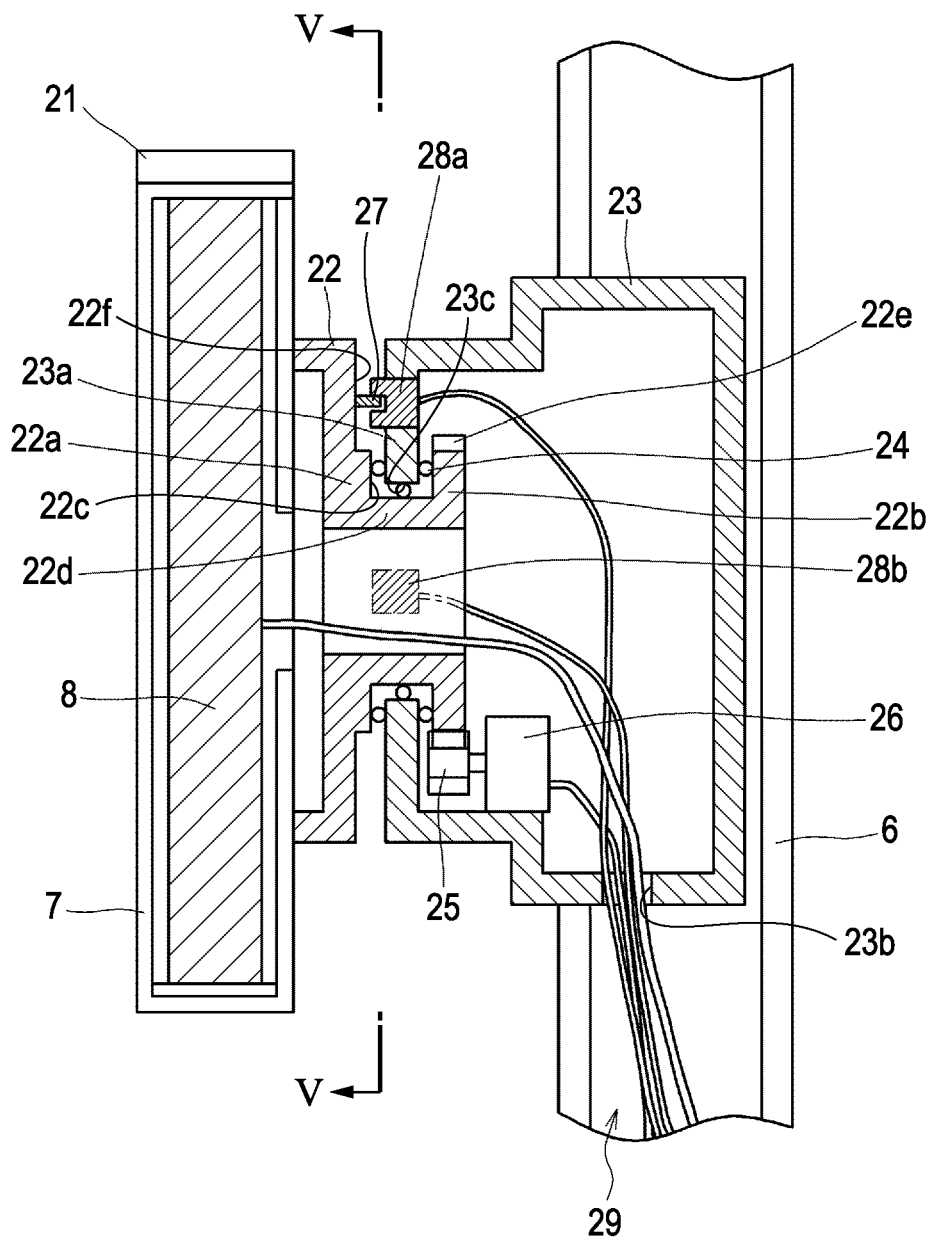
FIG. 4 is a cross-sectional view of an imaging unit and peripheral components.

FIG. 4 is a cross-sectional view of a supporting mechanism supporting the imaging unit 7. The back side of the imaging unit 7 containing the X-ray detector 8, which is the side opposite to the side facing the subject S, is mounted on a base 22 and further mounted on the platform 6 through a cradle 23 which is movable in the up and down directions relative to the platform 6. Flanges 22a and 22b are provided on the front and rear end portions of the base 22, respectively, forming a depression 22c having an angular U-shape in cross section. The flanges 22a and 22b and the depression 22c constitute a shaft portion 22d. The flange 23a of the cradle 23 is mounted in the depression 22c via a plurality of bearings 24. An external gear 22e is provided at the end of the flange 22b, which is located inside of the cradle 23. This external gear 22e is engaged with a gear 25 connected to an output shaft of a motor 26.

Further, a chopper 27 is provided on a surface 22f of the flange 22a. Photo-interrupters 28a and 28b, which correspond to the imaging unit orientation detector 9, are provided at two positions on the flange 23a of the cradle 23 which faces the chopper 27.

Figure 5:
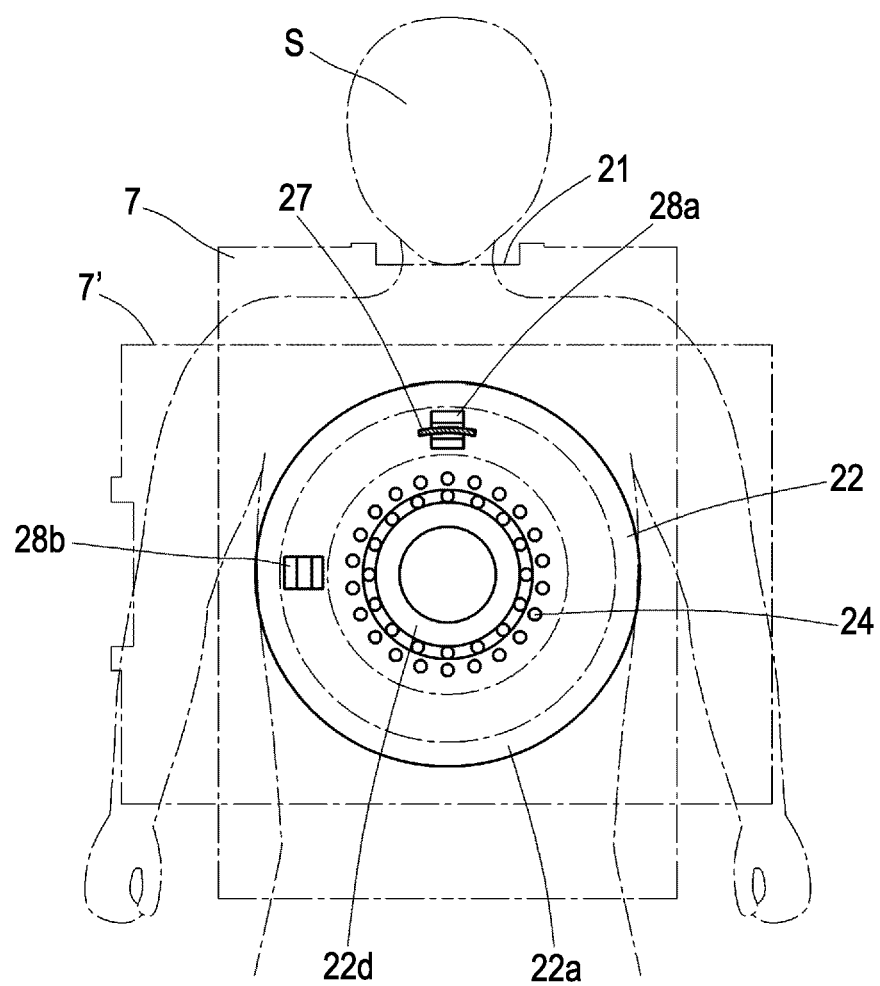
FIG. 5 is a cross-sectional view taken along line V-V shown in FIG. 4.

FIG. 5 is a cross-sectional view taken along line V-V in FIG. 4. As illustrated in FIG. 5, the photo-interrupter 28b is provided at a position shifted 90 degrees counterclockwise from the photo-interrupter 28a.

The X-ray detector 8, the motor 26, and the photo-interrupters 28a and 28b are connected to cables 29 which are wired within the platform 6 via a hole 23b provided in the cradle 23. These cables 29 extend inside the platform 6 and are connected to the system control unit 13 and the like. The cables 29 are used for driving components such as the imaging unit 7, the X-ray detector 8 contained in the imaging unit 7, the motor 26, and the photo-interrupters 28a and 28b, and for performing transmission of images and signals.

The flanges 22a and 22b, the shaft portion 22d, and the external gear 22e are components each having an axisymmetric part, with its central axis set in the direction perpendicular to the X-ray detecting surface of the apparatus. The cradle 23 supporting the base 22 has a tail end surface 23c facing the shaft portion 22d. This tail end surface 23c functions as a shaft bearing. A number of bearings 24 are provided between the base 22 and the cradle 23, realizing a shaft bearing function for smooth shaft rotation. The bearings 24 may be substituted by driven rollers having cylindrical or conical surfaces as in the case of various general shaft bearings, or may be sliding bearings, fluid bearings, or the like, to achieve similar effects.

Figure 6:
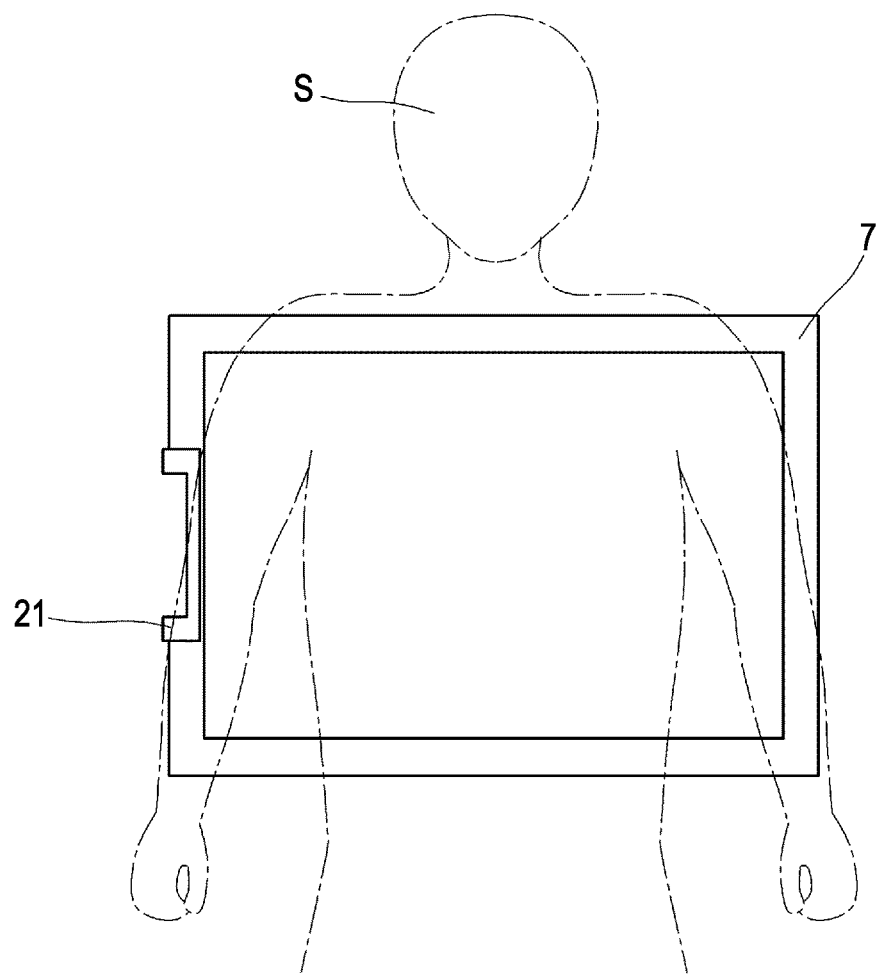
FIG. 6 is an elevational view illustrating an imaging unit rotated 90 degrees counterclockwise.

The above rotation mechanism allows the imaging unit 7 to rotate about the shaft portion 22d which is perpendicular to the X-ray detecting surface to change the orientation relative to the subject S, as indicated by imaging units 7 and 7' in FIG. 5. In particular, as illustrated in FIG. 6, a projection image including the entire body of the subject S can advantageously be obtained in the CBCT mode, by rotating the imaging unit 7 such that the short sides of the detection area are parallel to the longitudinal axis of the subject S. In the CBCT mode, in general, the subject S and the imaging unit 7 are not assumed to be in contact with each other. Thus, it is not necessary to avoid an increase in the transverse dimension of the imaging unit 7. Therefore, the dimension in the direction of the long sides can be set to be as large as necessary, unlike the case of the dimension in the direction of the short sides which has a restriction as described above.

The external gear 22e of the base 22 is engaged with the gear 25 provided at the output shaft of the motor 26. The rotation of the motor 26 permits the base 22 to rotate. The motor 26 is electrically connected to the system control unit 13 through the cables 29 to perform drive control according to need.

In this exemplary embodiment, the orientation of the imaging unit 7 can be rotated by 360 degrees. However, a freedom of rotation of at least 90 degrees, which allows the orientations of the imaging unit 7 indicated in FIG. 3 and FIG. 6, may be sufficient to meet most imaging requirements.

The photo-interrupters 28a and 28b are disposed at positions corresponding to the 90-degree rotation of the imaging unit 7. The chopper 27 is configured to interrupt the optical paths of the photo-interrupters 28a and 28b when brought to positions facing the photo-interrupters 28a and 28b, respectively. When the optical path of the photo-interrupter 28a or the photo-interrupter 28b is interrupted by the chopper 27, an ON signal is transmitted to the system control unit 13. When the chopper 27 comes away from the photo-interrupter 28a or the photo-interrupter 28b, the transmission of the ON signal is discontinued or transmission of an OFF signal is initiated.

The chopper 27 is set to activate the photo-interrupter 28a when the imaging unit 7 has the orientations illustrated in FIG. 3. That is, as illustrated in FIG. 5, the position of the chopper 27 coincides with that of the photo-interrupter 28a when the long sides of the imaging unit 7 are parallel to the longitudinal axis of the subject S and the chin rest 21 is set at the upper position. With this arrangement, the system control unit 13 can recognize that the chin rest 21 is located at the upper position.

When the position of the chopper 27 coincides with that of the photo-interrupter 28b, the short sides of the detection area are parallel to the longitudinal axis of the subject, as illustrated in FIG. 6, which can also be recognized by the system control unit 13.

While the photo-interrupters 28a and 28b are used in this exemplary embodiment, similar effects can be obtained when electrical switches are used in place thereof. In such a case, switches and members for operating the switches may be provided at the positions corresponding to the photo-interrupters 28a and 28b.

Although not illustrated in this exemplary embodiment, a locking mechanism may be provided to prevent unexpected rotation of the imaging unit 7 around the shaft portion 22d, which leads to an alteration in the orientation of the imaging unit 7. Such a locking mechanism realizes an imaging operation in a stable state even if the subject S comes into contact with the imaging unit 7.

Figure 7:
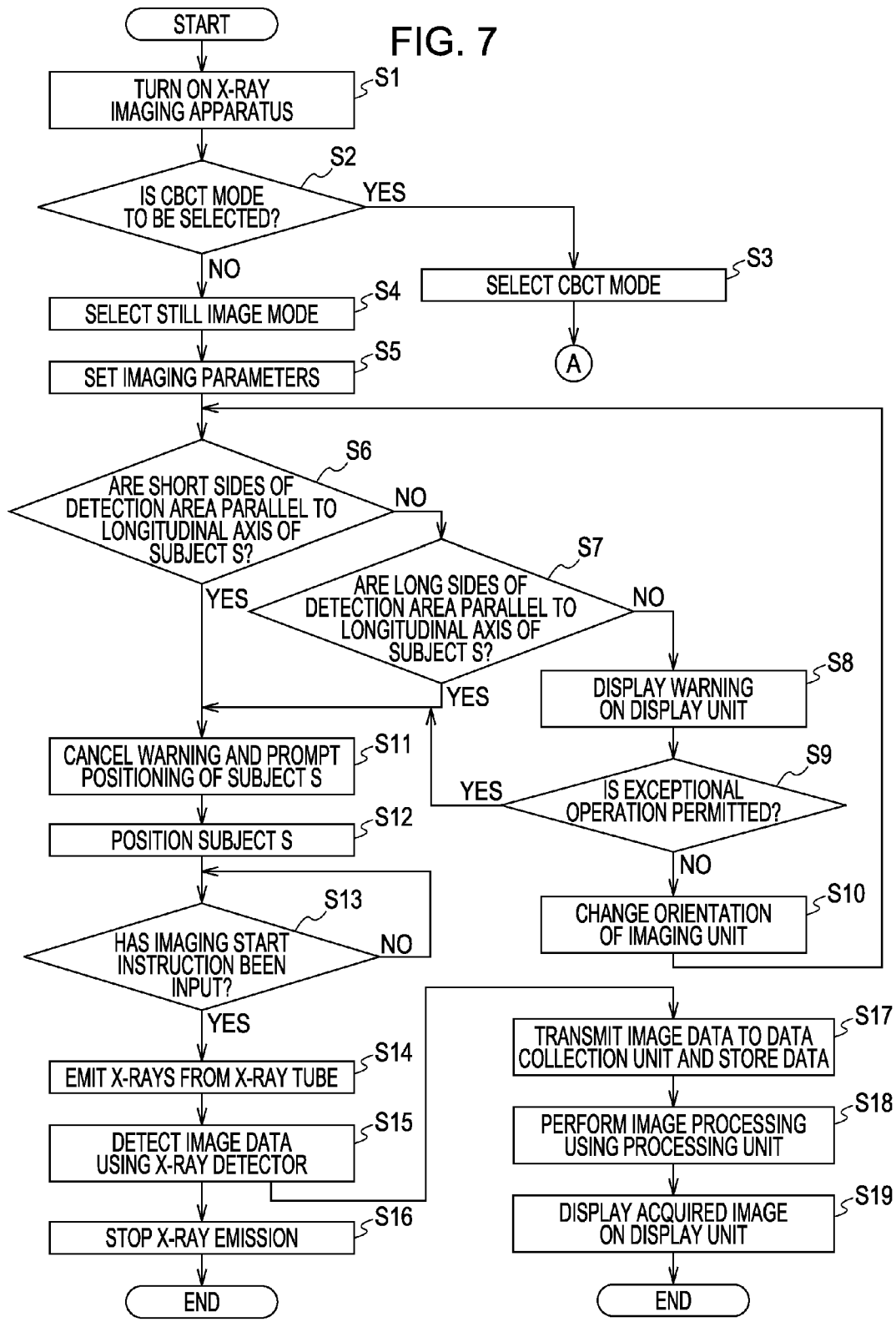
FIG. 7 is a flowchart illustrating an imaging procedure.
Figure 8:
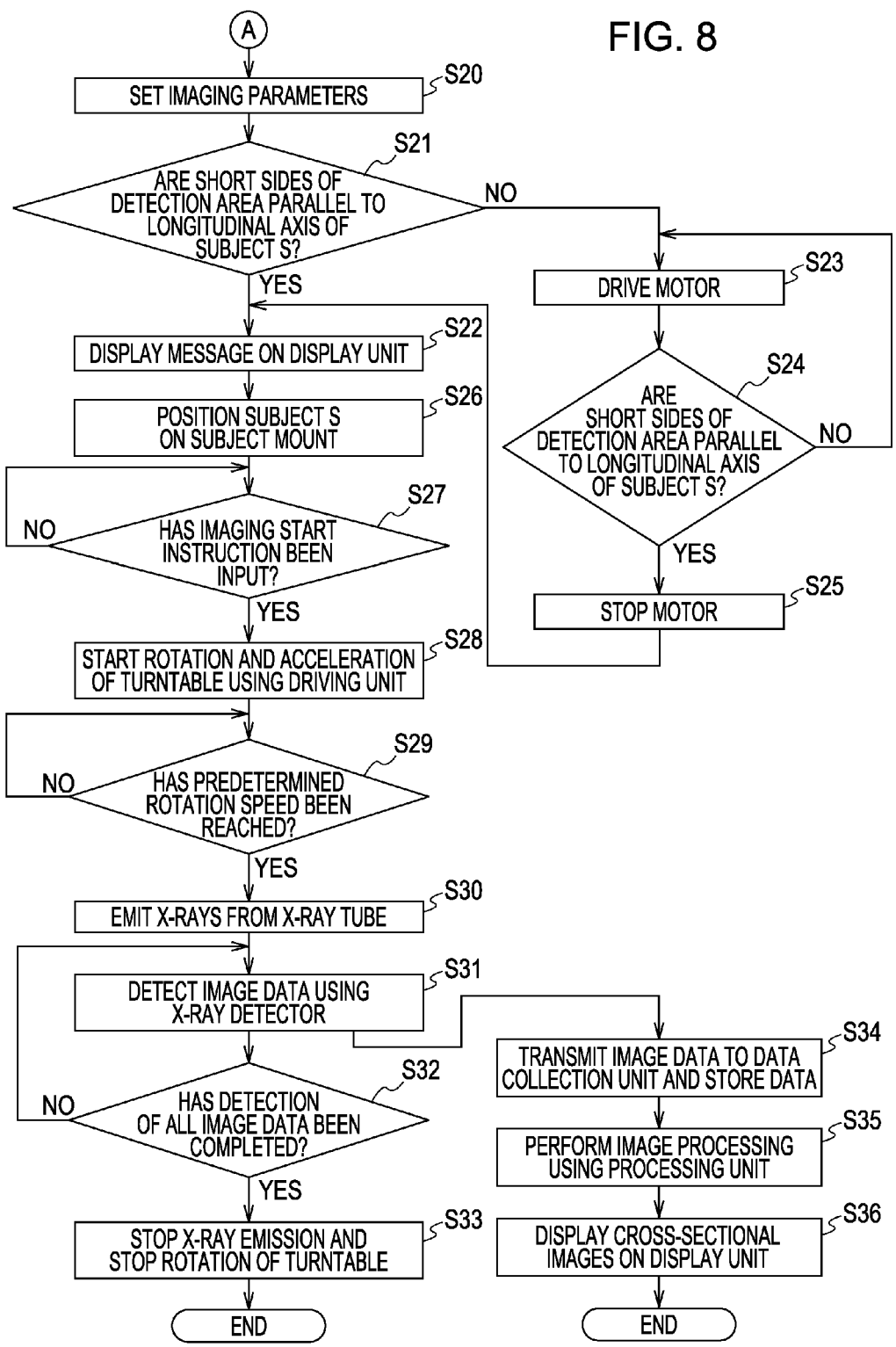
FIG. 8 is a flowchart illustrating an imaging procedure subsequent to A in FIG. 7.

FIGS. 7 and 8 are flowcharts illustrating an imaging procedure performed by the X-ray imaging apparatus described above. When the power of the X-ray imaging apparatus is turned on at Step S1, either a CBCT mode or a still image mode is determined at Step S2. When the CBCT mode is to be selected, the procedure proceeds to Step S3 and the subsequent procedure is illustrated in the flowchart in FIG. 8.

When the CBCT mode is not selected in Step S2, the procedure proceeds to Step S4 in which the still image mode is selected. At Step S5, various imaging parameters are set. Then, at Step S6, it is determined if the short sides of the detection area of the X-ray detector 8 are parallel to the longitudinal axis of the subject S. In this step, an output signal from the photo-interrupter 28b is checked. If the signal is in an ON state, the short sides of the detection area of the X-ray detector 8 are determined to be parallel to the longitudinal axis of the subject S. In this case, imaging is permitted, and the procedure proceeds to Step S11.

On the other hand, if, in Step S6, the short sides of the detection area of the X-ray detector 8 are determined to not be parallel to the longitudinal axis of the subject S, the procedure proceeds to Step S7. At Step S7, an output signal from the photo-interrupter 28a is checked, and it is determined whether or not the long sides of the detection area are parallel to the longitudinal axis of the subject S. If the long sides of the detection area are determined to be parallel to the longitudinal axis of the subject S, the procedure proceeds to S11.

In Step S7, if the photo-interrupter 28a is determined to be in an OFF state, it is determined that the longitudinal axis of the subject S is not parallel to any side of the rectangular detection area of the X-ray detector 8. This state leads to output of an image which is not satisfactory in terms of the angle of view, and thus the procedure proceeds to Step S8 in which a warning is displayed on the display unit 12 via a warning transmitter. This prevents an image operation being performed while unexpected changes in the position and orientation of the imaging unit 7 occur.

At Step S9, it is determined whether or not an imaging operation under such an exceptional condition as described above (exceptional imaging operation) is permitted. When the operator permits the exceptional imaging operation, indicating that the imaging procedure is to be continued, the procedure proceeds to Step S11. If the operator does not permit the exceptional imaging operation, the operator changes the orientation of the imaging unit at Step S10. In order to change the orientation of the imaging unit 7 in Step S7, the operator may input an instruction from the input unit 14 to control the rotation of the motor 26 or manually change the orientation of the imaging unit 7. When the orientation of the imaging unit 7 has been changed, the procedure returns to Step S6.

That is, if any one of the photo-interrupters 28a and 28b is determined to be in the ON state in Step S6 or Step S7, the procedure proceeds to Step S11. At Step S11, if the warning is displayed on the display unit 12, the warning is canceled, and a message indicating that preparation for positioning of the subject S has been completed, such as "Please position subject", is displayed.

The subject S is positioned at the subject mount 1 at Step S12, and it is determined if an imaging start instruction has been input. When the operator inputs the imaging start instruction using the input unit 14, the procedure proceeds to Step S14. At Step S14, X-rays are emitted from the X-ray tube 5 toward the subject S under predetermined irradiation conditions. At Step S15, the X-ray detector 8 detects an X-ray projection image. Immediately after the detection is completed, the irradiation of X-rays is discontinued at Step S16 and the imaging procedure is terminated.

The image data detected in Step S15 is transmitted to and stored in the data collection unit 10 at Step S17. Then, the image data is appropriately processed by the processing unit 11 at Step S18. Subsequently, the image acquired in the processing of Step S18 is displayed on the display unit 12 at Step S19, so that the operator can obtain information necessary for diagnosis and observation.

If, in Step S3, the CBCT mode is selected, the procedure proceeds to Step S20 and various imaging parameters are set using the input unit 14. Then, at Step S21, an output signal from the photo-interrupter 28b is checked. The ON state of the photo-interrupter 28b indicates that the short sides of the detection area of the X-ray detector 8 are parallel to the longitudinal axis of the subject S, which is suitable for CBCT imaging. In this case, the procedure proceeds to Step S22.

If, in Step S21, the short sides of the detection area of the X-ray detector 8 are determined to not be parallel to the longitudinal axis of the subject S, control of rotation of the motor 26 is initiated at Step S23. Then, at Step S24, it is determined whether or not the short sides of the detection area of the X-ray detector 8 are parallel to the longitudinal axis of the subject S. The processing of Step S23 and Step S24 is repeated until the short sides of the detection area of the X-ray detector 8 have been determined to be parallel to the longitudinal axis of the subject S. When the photo-interrupter 28b enters the ON state, the rotation of the motor 26 is discontinued at Step S25.

Through the above procedure, the apparatus has entered the appropriate state for CBCT imaging, and the procedure proceeds to Step S22 to inform the operator of the state. At Step S22, a message such as "Please position subject" is displayed on the display unit 12.

At Step S26, the subject S is positioned on the subject mount 1 using the subject supporting member 4. At Step S27, it is determined whether or not an imaging start instruction has been input by the operator using the input unit 14. If it is determined that the imaging start instruction has been input, the driving unit 2 starts and accelerates rotation driving of the turntable 3 at Step S28.

At Step S29, it is determined if the turntable 3 has reached a predetermined rotation speed. If it is determined that the turntable 3 has reached the predetermined rotation speed, the procedure proceeds to Step S30, and if not, the processing of Step S29 is repeated until the predetermined rotation speed has been reached.

At Step S30, X-rays are emitted from the X-ray tube 5 onto the subject S under predetermined irradiation conditions. Then, at Step S31, the X-ray detector 8 starts detection of an X-ray projection image. X-ray projection image data of the body section of the subject S arranged within the X-ray irradiation area and corresponding area of the subject supporting member 4 is detected in sequence for each predetermined angle of the turntable 3.

At Step S32, it is determined whether or not all X-ray projection image data has been detected. That is, when the turntable 3 has rotated 360 degrees and all X-ray projection image data to be detected in one imaging operation has been detected, the procedure proceeds to Step S33. At Step S33, the irradiation of X-rays is immediately discontinued, and at the same time the rotation of turntable 3 is decelerated and discontinued. Then, the imaging procedure is terminated.

At Step S34, a volume of the image data detected in Step S31 which corresponds to predetermined angles of the turntable 3 is transmitted to and stored in the data collection unit 10. At Step S35, the processing unit 11 performs reconstruction of the image data. At Step S36, a resultant cross-sectional image and three-dimensional image are displayed on the display unit 12, so that the operator can obtain information necessary for diagnosis and observation.

In this exemplary embodiment, the orientation of the imaging unit 7 can be changed automatically by the motors 26. However, for simplification and cost reduction of the apparatus, the motor 26 may be omitted and the orientation of the imaging unit 7 may be altered manually. In such a case, a message such as "Change orientation of imaging unit" is displayed on the display unit 12, instead of driving the motor 26 in Step S23 to achieve similar effects.

As described above, in the X-ray imaging apparatus according to an exemplary embodiment of the present invention, the orientation of the imaging unit 7 may be selected from among at least two orientations; the first orientation in which the long sides of the detection area of the X-ray detector 8 are parallel to the longitudinal axis of the subject S, and the second orientation in which the short sides of the detection area of the X-ray detector 8 are parallel to the longitudinal axis of the subject S. This allows the apparatus to be used for both CT imaging and still imaging under desirable imaging conditions.

The above exemplary embodiment has described a case of CT imaging in which imaging is performed by rotating the subject S on the turntable 3 while the imaging system composed of the X-ray tube 5 and the X-ray detector 8 remains in a static position. However, since similar CT imaging can be performed based on relative movement between an imaging system and a subject, the part that is to be rotated may be set in the other way. That is, a supporting member such as a C-Arm supporting both the X-ray tube 5 and the X-ray detector 8 may be relatively rotated around the subject S being in a static position. In this case, the turntable 3 for fixing the subject S is not necessary, and the driving unit 2 may be connected to a supporting member supporting both the X-ray tube 5 and the imaging unit 7 to transmit rotation force. Thus, the present invention may be applicable to such general CT imaging using a so-called C-Arm imaging device.

In CT imaging for capturing cross-sectional images and three-dimensional images, an X-ray imaging apparatus according to an exemplary embodiment of the present invention permits imaging of a patient having a large body width, for example, with an increased transverse dimension of the detection area. In capturing still images of the chest or the like, the transverse dimension of the housing of the imaging unit may be decreased, which not only allows the body section from the chest to the shoulder to come into contact with the front surface of the imaging unit but also stabilizes the posture of the patient. This realizes imaging operations under desirable conditions in both CT imaging and still imaging of the chest and thus realizes satisfactory images.

While the present invention has been described with reference to exemplary embodiment, it is to be understood that the invention is not limited to the disclosed exemplary embodiment. The scope of the following claims is to be accorded the broadest interpretation so as to encompass all modifications and equivalent structures and functions.

This application claims priority from Japanese Patent Application No. 2008-205689 (Aug. 8, 2008) filed on Aug. 8, 2008, the entire contents of which are hereby incorporated by reference herein.

What is claimed is:

1. An X-ray imaging apparatus, comprising:
   a support member for rotatably supporting an X-ray detector for detecting X-ray radiation to obtain an X-ray image;
   a selector for selecting an imaging mode of the X-ray imaging apparatus; and
   a warning transmitter for transmitting a warning in a case that the X-ray detector is not supported in a manner corresponding to the selected imaging mode.

2. The X-ray imaging apparatus of claim 1, further comprising:
   a control unit configured to operate the X-ray imaging apparatus in the selected imaging mode,
   wherein the X-ray detector supported by the support member is movable between at least a first orientation and a second orientation, and
   wherein the warning transmitter is configured to output a warning when imaging is initiated in a state that the X-ray detector is oriented in neither the first orientation nor the second orientation.

3. The X-ray imaging apparatus of claim 2, further comprising:
   a receiving unit configured to receive information input by a user indicating whether or not imaging operation is permitted when the X-ray detector is oriented in neither the first orientation nor the second orientation.

4. The X-ray imaging apparatus of claim 3, wherein the control unit permits operation of the X-ray imaging apparatus in the selected imaging mode, in response to the input of information indicating that imaging operation is permitted when the X-ray detector is oriented in neither the first orientation nor the second orientation.

5. The X-ray imaging apparatus of claim 3, wherein the warning transmitter stops outputting the warning, in response to the input of information indicating that imaging operation is permitted when the X-ray detector is oriented in neither the first orientation nor the second orientation.

6. The X-ray imaging apparatus of claim 4, further comprising:
   a changing unit configured to change an orientation of the X-ray detector into the orientation corresponding to the selected imaging mode, in response to the input of information indicating that imaging operation is not permitted when the X-ray detector is oriented in neither the first orientation nor the second orientation.

7. The X-ray imaging apparatus of claim 2, further comprising:

an orientation detector configured to detect an orientation of the X-ray detector supported by the support member, wherein the control unit permits operation of the X-ray imaging apparatus in a still imaging mode when the detected orientation is the first orientation.

8. The X-ray imaging apparatus of claim 2, wherein the warning transmitter outputs the warning when the imaging is initiated in a computed tomography imaging mode and the X-ray detector is oriented in the first orientation.

9. The X-ray imaging apparatus of claim 2, further comprising:

an orientation detector configured to detect the orientation of the X-ray detector, wherein the control unit permits operation of the X-ray imaging apparatus in a computed tomography imaging mode when the detected orientation is the second orientation.

10. The X-ray imaging apparatus of claim 2, wherein the warning transmitter outputs the warning when the imaging is initiated in a still imaging mode and the X-ray detector is oriented in the second orientation.

11. The X-ray imaging apparatus of claim 2, further comprising:

an orientation detector configured to detect the orientation of the X-ray detector, wherein the control unit permits operation of the X-ray imaging apparatus in a still imaging mode when the detected orientation is the first orientation, and wherein the control unit permits the operation of the X-ray imaging apparatus in a computed tomography imaging mode when the detected orientation is the second orientation.

12. The X-ray imaging apparatus of claim 2, further comprising an X-ray generator; and a driving unit configured to relatively rotate the X-ray generator and the X-ray detector around a subject when the X-ray imaging apparatus operates in a computed tomography imaging mode.

13. The X-ray imaging apparatus of claim 1, wherein the X-ray detector defines a rectangular detection area having short sides and long sides, wherein the X-ray detector is movable between a first orientation and a second orientation, wherein, in the first orientation, the long sides of the rectangular detection area are parallel to a longitudinal axis of a subject, and wherein, in the second orientation, the short sides of the detection area are parallel to the longitudinal axis of the subject.

14. The X-ray imaging apparatus of claim 1, wherein the X-ray detector defines a rectangular detection area, and wherein the warning transmitter outputs the warning except when either of the sides of the rectangular detection area is substantially parallel to a longitudinal axis of a subject.

15. The X-ray imaging apparatus of claim 1, further comprising:

an orientation detector configured to detect an orientation of the X-ray detector in response to the selection, wherein the selector is configured to select one imaging mode out of a computed tomographic imaging mode and a still imaging mode.

16. A C-arm X-ray imaging device, comprising:

an X-ray detector defining a rectangular detection area and configured to be movable between at least a first orientation and a second orientation;

an X-ray generator;

a selection unit configured to select an imaging mode;

an orientation detector configured to detect an orientation of the X-ray detector in response to the selection by the selection unit;

a control unit configured to selectively operate the C-arm X-ray imaging device in either a computed tomographic imaging mode or a still imaging mode;

a driving unit configured to relatively rotate the X-ray generator and the X-ray detector around a subject when the C-arm X-ray imaging device operates in the computed tomography imaging mode;

a warning unit configured to output a warning when imaging is initiated, wherein the warning unit outputs a warning except when either of the sides of the rectangular detection area is substantially parallel to a longitudinal axis of the subject; and a receiving unit configured to receive information input by a user indicating whether or not imaging operation is permitted when the X-ray detector is oriented in neither the first orientation nor the second orientation, wherein the control unit permits operation of the X-ray imaging apparatus in the selected imaging mode in response to the input of information indicating that imaging operation is permitted when the X-ray detector is oriented in neither the first orientation nor the second orientation.

17. A method of operating an X-ray imaging apparatus for detecting X-ray radiation to obtain an X-ray image, the X-ray imaging apparatus including a support member for movably supporting an X-ray detector in at least one of a plurality of imaging modes of the X-ray imaging apparatus, the method comprising:

detecting an orientation of the X-ray detector;

selecting an imaging mode of the X-ray imaging apparatus;

determining whether the detected orientation corresponds to the selected imaging mode; and outputting a warning in a case that the detected orientation is determined as not corresponding to the selected imaging mode.

* * * * *